Figure 1:
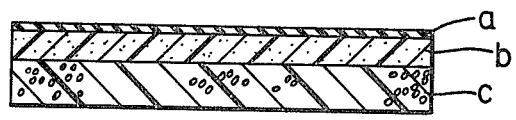

United States Patent [19]

Klemm et al.

[11] 4,191,743

[45] Mar. 4, 1980

[54] ANTIBACTERIAL WOUND DRESSING

[75] Inventors: Klaus Klemm; Helmut Wahlig, both of Darmstadt, Fed. Rep. of Germany

[73] Assignee: Merck Patent Gesellschaft mit beschrankter Haftung, Darmstadt, Fed. Rep. of Germany

[21] Appl. No.: 847,868

[22] Filed: Nov. 2, 1977

[30] Foreign Application Priority Data

Nov. 2, 1976 [DE] Fed. Rep. of Germany ....... 2650306

[51] Int. Cl.² .................... A61F 13/00; A61F 7/02; A61L 15/03

[52] U.S. Cl. ........................................ 424/28; 424/81; 128/156; 128/280

[58] Field of Search .................... 424/28, 81; 128/156, 128/260

[56] References Cited

U.S. PATENT DOCUMENTS

| 2,430,740 | 11/1947 | Sharples | 424/28 |
|---|---|---|---|
| 3,055,297 | 9/1962 | Leeds | 424/28 X |
| 3,551,556 | 12/1970 | Kument et al. | 424/81 X |
| 3,598,122 | 8/1971 | Zaffaroni | 424/28 X |
| 3,641,237 | 2/1972 | Gould et al. | 424/81 X |
| 3,648,692 | 3/1972 | Wheeler | 128/156 |
| 3,660,563 | 5/1972 | Gould et al. | 424/81 |
| 3,857,932 | 12/1974 | Shepherd et al. | 424/81 |
| 3,881,026 | 4/1975 | Shepherd et al. | 424/81 |
| 3,882,858 | 5/1975 | Klemm | 128/92 G |
| 4,059,684 | 11/1977 | Gross et al. | 424/81 X |

OTHER PUBLICATIONS

C.A. 82:103178m (1975), 81 #29549u (1974), 86 #47277m, #34247b, #47297t (1977).

*Primary Examiner*—Shep K. Rose
*Attorney, Agent, or Firm*—Millen & White

[57] ABSTRACT

Antibiotics can be effectively administered to wounds over long time periods by a wound dressing which comprises at least two layers of synthetic resin arranged one above the other and an intermediate layer composed of a synthetic resin granulate (particle size: 0.5–3mm) having an antibiotic incorporated therein.

5 Claims, 6 Drawing Figures

ANTIBACTERIAL WOUND DRESSING

BACKGROUND OF THE INVENTION

The present invention concerns an antibacterial wound dressing, consisting of several layers of synthetic resin material arranged one above the other and an intermediate layer containing an antibiotic.

A similar wound dressing, per se, is known from published German patent specification No. 21 03 590. However, this wound dressing suffers from a decisive disadvantage in that it does not act antibacterially. This failure is significant since for most wounds, especially in the case of large area burns, infection, next to fluid loss, represents the greatest danger for the patient and requires a high-dosed and long-lasting parenteral antibiotic treatment.

In attempts to overcome this disadvantage, wound dressings have been impregnated with antibiotic-containing solutions. However, because of the too low concentration of the antibiotic which is produced in this way, this technique has not been successful. Similarly, the process suggested in published German patent specification No. 21 03 590, i.e., applying an antibiotic-containing salve to the side of the dressing facing, is not suitable because the salve can only be thinly distributed and, therefore, as above, the antibiotic concentration is too low. Moreover, with the known processes, a long-lasting local antibacterial action also cannot be achieved.

SUMMARY OF THE INVENTION

Accordingly, it is an object of this invention to provide a wound dressing which has a high antibacterial effectiveness and is able to provide an antibiotic to the wound site in satisfactorily high dosage and for sufficiently long periods of time.

Upon further study of the specification and appended claims, further objects and advantages of this invention will become apparent to those skilled in the art.

These objects have been attained by incorporating the antibiotic in the wound dressing in the form of a synthetic resin granulate.

Thus, in a composition aspect, this invention provides an antibacterial wound dressing, comprising at least two layers of synthetic resin material lying on top of one another and an intermediate layer containing an antibiotic, wherein the antibiotic is incorporated into a synthetic resin granulate having a particle size of 0.5–3 mm.

In a method of use aspect, the present invention relates to a method of administering an antibiotic to a wound which comprises dressing the wound with the wound dressing of this invention.

DETAILED DISCUSSION

The antibiotic-containing synthetic resin granulate of this invention is based upon polymethacrylates and/or polyacrylates and contains at least one antibiotic. Preferably, the granulate contains essentially a copolymer of methacrylic acid methyl ester and methyl acrylate. As antibiotic, the granulate preferably contains gentamycin.

Synthetic resins based on polymethacrylates and/or polyacrylates suitable for surgical purposes are known, for example from U.S. Pat. No. 3,882,858. Very conventional is, for example, a bone cement which, in a standard pack, contains two sachets each with about 40 g. of powder and 2 ampoules each with 20 ml. of liquid. This product is commercially available as PALACOS, especially PALACOS R, manufactured by KULZER & CO., Bad Homburg, Federal Republic of Germany. The powder is a fine pearl polymerisate (particle diameter <30 μm) of methacrylic acid methyl ester with a copolymer proportion of methacrylate. As catalyst, about 0.5% dibenzoyl peroxide is added to the powder. For purposes of characterizing the material, traces of chlorophyll are copolymerized during production. The liquid consists of monomeric methacrylic acid methyl ester, to which are added, as accelerator, about 0.7% dimethyl-p-toluidine, and traces of hydroquinone as stabilizer. As a rule, this liquid is also colored with traces of chlorophyll for characterization purposes. The powder packed into polyethylene sachets is sterilized with ethylene oxide. The liquid is steril filtered and filled into glass ampoules.

When 2 parts by wt. of powder are mixed with 1 part by wt. of liquid, the dibenzoyl peroxide reacts with the dimethyl-p-toluidine in the liquid, whereby the radical polymerization is initiated. The mixing is so adjusted that the product can be used as a paste after only about one minute. This paste remains kneadable for about 4 minutes and then begins to harden, with the evolution of heat. After 6 minutes, the polymerization is substantially complete. During the elastic phase, the paste is shaped so that the desired form is obtained. The so-shaped granulate, i.e., spheroidal, of this invention should possess, as far as possible, a uniform surface and uniform particle diameter. The granulate can also be produced by comminution of the hardened material and sieving out of the desired sized particles or by other conventional techniques used for the production of synthetic resin granulates. This known bone cement material is preferred for the production of the synthetic resin granulate in the wound dressing of this invention.

The particle diameter of the granulate should be between 0.5 and 3 mm., preferably at about 1 mm. Thereby, on the one hand, the antibiotic contained therein is dissolved into the wound secretion in a concentration sufficient for combating the infection and, on the other hand, no unevenness in pressure or coverage of the wound is caused by large particles. This is important since the object of the treatment is to provide an infection- and necrosis-free wound base which is as smooth as possible in order that, e.g., a subsequent skin graft can be preformed with as low a risk as possible for the final removal of the defect wound.

According to this invention, the particles of the granulate are preferably connected mesh-like to one another by threads or wires. For example, this can be accomplished by pressing a mesh of threads or wire into the material when it is still in a formable state. Suitable threads include surgical stitching material of silk, synthetic resins or high alloy steel. Preferably, monofile or polyfile (i.e., several wires twisted together) surgical wire, of a high alloy steel which is permissible for use in medicine, is used. The monolayer of the synthetic resin granulate so produced has the advantage that it can be easily introduced between the layers of the synthetic resin material in the dressing, and before the polymerization is complete, can easily be bound to the synthetic resin layers arranged above and below it. The wound dressing of this invention then remains very elastic and supple.

Before mixing the components in the production of the synthetic resin granulate, an antibiotic is admixed therewith. The incorporation of the antibiotic into the granulate is conventional and is disclosed, for example, in U.S. Pat. No. 3,882,858 and German patent specification No. 2,511,122. In principle, all antibiotics are suitable as long as they are not damaged by the temperatures occurring during the hardening of the paste and are liberated in the desired manner from the synthetic resin. Since, however, the polymerization results in small particles which have a comparatively large surface and thus permit good removal of the resulting heat of polymerization, this heat tolerance property is not critical. In principle, all antibiotics—alone or as mixtures—can be used if they are substantially thermostable at the temperatures occurring during the polymerization. That is, they typically should withstand temperatures from about 60° to 80° C., without substantial loss of activity. Furthermore, the antibiotics should be chemically stable towards the synthetic resin. Their spectrum of activity includes gram-positive and/or gram-negative microorganisms, preferably both types. If possible, the microorganism to be treated should exhibit a retarded resistance development with regard to the antibiotics used. From the large number of possible antibiotics, the following are typical: erythromycin, lincomycin, clindamycin, novibiocin, vancomycin, fusidic acid, rifampicin, polymyxins, neomycin, kanamycin, tobramycin and, especially, gentamycin. Penicillins and cephalosporins are also suitable. The aminoglycoside antibiotics are especially suitable because of their broad antibacterial spectrum and their heat stability.

Gentamycin, e.g., is an aminoglycoside antibiotic which acts preponderantly bactericidally against gram-positive and, especially, gram-negative microorganisms. Furthermore, it is known that gentamycin is especially advantageously liberated, particularly from synthetic resins based on polymethacrylates and/or polyacrylates. The very good water solubility of this antibiotic has a very favorable influence upon its diffusion from the synthetic resin. This high diffusability makes possible an almost constant liberation of the antibiotic which decreases only slowly over a long period of time.

The amount of the antibiotic to be added can be varied within wide ranges and depends substantially upon the activity of the antibiotic. In general, the amount of antibiotic is about 0.2 to 15 wt. %, referred to the weight of the granulated polymer. For gentamycin, amounts between 1 and 4 wt. % (calculated on a gentamycin base) have proven to be especially favorable. However, other antibiotics or mixtures of antibiotics can also be used and the suitable preparations thereof which are adequate for effective antimicrobial activity can be determined by routine considerations. If the cause of the disease or the resistance of a microorganism towards the incorporated antibiotic changes, the wound dressing of this invention can, of course, be removed and possibly replaced by another one which contains a granulate having other antibiotics which are more effective. The antibiotic-containing granulate is generally applied between the layers of the dressing.

Several preferred embodiments of the wound dressing of this invention are illustrated in FIGS. 1–6. The Figures show cross-sections of the wound dressing not drawn to scale.

The layers are designated as (a) to (d). The individual layers can be characterized as follows:

(a) is a layer of microporous synthetic resin material which is gas-permeable and liquid impermeable. Suitable materials for this layer include natural and synthetic rubber materials, perferably polytetrafluoroethylene foils or polypropylene foils. The layer thickness is generally about 25 to 150 μm. The pore size should lie in the range of about 0.1 to 0.5 μm.

(b) is the layer of synthetic resin granulate into which the antibiotics are incorporated. The layer thickness is generally about 0.5 to 3 mm., preferably about 1 mm.

(c) is a layer of open-celled foamed material. Suitable such materials include neutral, physiologically compatible, foamable synthetic resins, preferably cross-linked polyurethane sponge or foam and also foamed synthetic resins based on urea-formaldehyde or melamine-formaldehyde or mixtures thereof. Furthermore, high molecular weight natural materials, such as collagen, are also suitable. The cell size should generally be about 50 to 200 μm. The layer thickness of the foamed material generally is between 0.5 and 10 mm., preferably between 0.5 and 7 mm.

(d) is a layer of open-celled foam material with a cell size below 50 μm., preferably between 10 and 40 μm. Suitable materials include those described for layer (c). The layer thickness is generally about 0.3 to 2 mm.

Details of the construction and composition of the conventional layer of the dressings of this invention are known and are disclosed, for example, in German patent No. 21 03 590, whose disclosure is incorporated by reference.

The layer (a) of microporous synthetic resin material serves as a covering layer for the side of the dressing remote from the wound. This layer serves substantially to prevent the loss of body fluid and to reduce or prevent the penetration of bacteria from the surroundings. The layer (c) of open-celled foamed material is absorbent and serves, in particular, for the absorption of cell debris and liquid exudate. The layer (d) of small-pore foamed material faces the wound and serves to avoid possible growth of fibroblasts through the open-celled foamed material. In this way, it is possible to leave the dressing on the wound for a comparatively long time without the wound bed being considerably damaged upon removal of the dressing.

FIG. 1 shows the cross-section of a wound dressing, wherein the layer of antibiotic-containing synthetic resin granulate (b) is arranged between the layers of microporous synthetic resin material (a) and open-celled foamed material (c).

Figure 2:
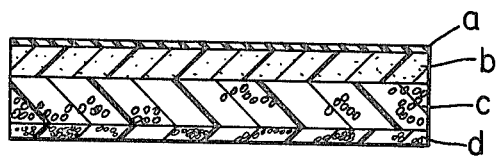

FIG. 2 contains, on the side of the wound dressing facing the wound, an additional layer (d) of open-celled, narrow-pore foamed material.

Figure 3:
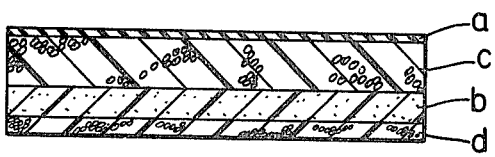

FIG. 3 shows an arrangement of the layers in which the layer of antibiotic-containing synthetic resin granulate (b) is arranged between the layers of open-celled foamed material having different pore sizes (c) and (d).

Figure 4:
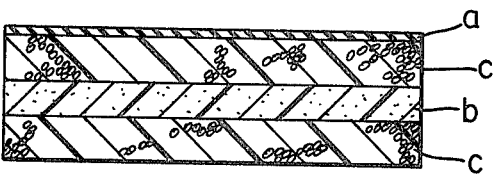

In FIG. 4, the layer (d) of FIG. 3 facing the wound is replaced by a layer (c).

Figure 5:
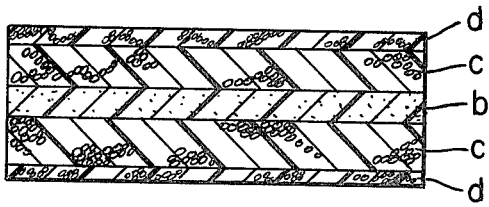

In FIG. 5, the layer of antibiotic-containing synthetic resin granulate (b) is arranged between two layers of open-celled foamed material (c) on each of which is fixed a further layer of narrow-pore foamed material (d). On the side of the dressing remote from the wound, the layer (d) can also be omitted or it can be replaced by the layer (a).

Figure 6:
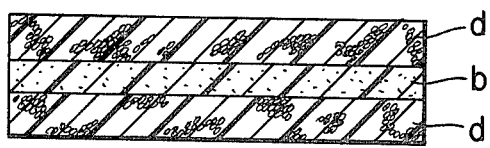

FIG. 6 shows an arrangement of the layers in which the layer of antibiotic-containing synthetic resin granulate (b) is arranged between two layers of narrow pore foamed material (d). In this case, it is advantageous to select a greater layer thickness for layer (d), e.g., up to 10 mm. The layer (d) remote from the wound can also be replaced by the layer (c).

The production of the antibacterially-acting wound dressing is accomplished by embedding the antibiotic-containing synthetic resin granulate between the appropriate layers. For example, this can be achieved by incorporating the granulate into the open-celled foamed material or by applying it to the side of the foamed material remote from the wound and subsequently placing thereon a foil of microporous synthetic resin material. It is also possible to apply the granulate to the foil of microporous synthetic resin material before it is combined with the layer of foamed material. Alternatively, the aforementioned mesh- or lattice-like intermediate layer of granulate can be inserted between the layers of foamed material and microporous synthetic resin material or between the layers of foamed material. This method is especially advantageous because the mesh or lattice of granulate can be produced in band form and easily introduced according to the desired dosage. The individual layers can be joined to each other, e.g., with an adhesive or by thermal melting. The wound dressing of this invention is usable for many types of defect wounds of the skin, such as, e.g., skin defects due to cut, tear and burst wounds, skin scraping, burns, frost bites and throphic ulcers. The wound dressing is useable not only as a temporary skin replacement for fresh, potentially infected skin injuries, i.e., as an infection prophylaxis, but also for the treatment of infection in the case of infected skin defect wounds and/or where a dressing is required, especially for extensive skin scraping or burns.

The antibiotics contained in the wound dressing are slowly and constantly liberated through the layer of the open-celled foamed material into the wound secretion. Even after some days, a good antibacterial effect is still present. This favorably influences healing by inhibition of infection.

The wound dressing can be produced in the form of areas of any desired size and/or shape from which pieces of suitable size and shape can be cut out according to requirements. The finished product is advantageously packed sterile in roll form of various widths. Pre-cut areas of different size which can be sealed in sterile fashion into aluminum or synthetic resin foils are also suitable.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

40 g. of a sterile, fine pearl polymerizate (particle diameter <30 μm), consisting of a copolymer of methacrylic acid methyl ester and methyl acrylate, which additionally contains 0.5% of dibenzoyl peroxide and traces of chlorophyll, are well mixed with 0.5 g. of gentamycin sulphate. The powder obtained is then mixed with 20 ml. of a liquid which consists of monomeric methacrylic acid methyl ester with an addition of about 0.7% of dimethyl-p-toluidine and about 0.006% of hydroquinone. From the paste resulting after thorough mixing, there are formed spheroids with a diameter of about 1 mm. After about 6 minutes, the particles are hardened. Optionally, the particles can be sterilized, e.g., by gassing with ethylene oxide. Still before complete hardening, the particles obtained are arranged in a closely packed monolayer and a net of threads or wire is pressed therein. This intermediate layer, preferably before completion of polymerization, is introduced between the layers of synthetic resin material, with which it is lightly joined by the use of pressure.

The wound dressing obtained is packed sterilely. When used, the side with the foamed material layer is applied directly to the wound.

EXAMPLE 2

Analogously to Example 1, a polymerizate is produced which, after complete hardening, is comminuted. From the granulate so obtained, particles are sieved out with a uniform size of about 1 mm. The particles are arranged in a closely packed monolayer or caused to soften with gentle warming. A mesh of threads or wires is pressed into the layer and subsequently the layer thus obtained is introduced between the layers of synthetic resin material.

The preceding examples can be repeated with similar success by substituting the generically or specifically described reactants and/or operating conditions of this invention for those used in the preceding examples.

For the foregoing description, one skilled in the art can easily ascertain the essential characteristics of this invention, and without departing from the spirit and scope thereof, can make various changes and modifications of the invention to adapt it to various usages and conditions.

What is claimed is:

1. A sterile wound dressing comprising two layers of synthetic resin arranged one above the other and an intermediate layer of an antibiotic within hardened, formed spheroids of a synthetic resin granulate, having a particle size of 0.5-3 mm., wherein the synthetic resin granulate comprises a copolymer of methacrylic acid methyl ester and methyl acrylate, and the antibiotic is selected from gentamycin, neomycin, kanamycin, tobramycin or other aminoglycoside antibiotics, erythromycin, lincomycin, clindamycin, novibiocin, vancomycin, fusidic acid, rifamycin, polymyxins, penicillins, and caphalosporins.

2. The wound dressing of claim 1, wherein the synthetic resin granulate has a particle size of about 1 mm.

3. A wound dressing of claim 1, wherein the synthetic resin granulate is arranged as a closely packed layer between the layers of synthetic resin material.

4. The wound dressing of claim 1, wherein the antibiotic is gentamycin.

5. A method of administering an antibiotic to a wound which comprises dressing the wound with the sterile wound dressing of claim 1.

* * * * *